(12) United States Patent
Heine et al.

(10) Patent No.: US 7,507,927 B2
(45) Date of Patent: Mar. 24, 2009

(54) BATTERY GRIP

(75) Inventors: Oliver Heine, Herrsching (DE); Dirk Schade, Penzberg (DE); Anton Schneider, Gilching (DE); Stefan Knesewitsch, Herrsching (DE); Georg Pfaffenbauer, Herrsching (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 0 days.

(21) Appl. No.: 11/937,560

(22) Filed: Nov. 9, 2007

(65) Prior Publication Data

US 2008/0110741 A1 May 15, 2008

(30) Foreign Application Priority Data

Nov. 13, 2006 (DE) .................. 10 2006 054 068

(51) Int. Cl.
*H01H 15/06* (2006.01)
(52) U.S. Cl. ..................................... 200/551
(58) Field of Classification Search ............ 200/551, 200/547, 537, 60, 559
See application file for complete search history.

(56) References Cited

U.S. PATENT DOCUMENTS 3,061,776 A * 10/1962 Rosenstrach ............... 324/506
3,071,747 A * 1/1963 Moore ....................... 338/179
3,297,840 A * 1/1967 Gray et al. .................. 200/60
3,643,083 A 2/1972 Heine
4,866,228 A 9/1989 Kamishima

* cited by examiner

*Primary Examiner*—Edwin A. Leon
(74) *Attorney, Agent, or Firm*—Bachman & LaPointe, P.C.

(57) ABSTRACT

A battery grip for diagnostic units comprises a grip sleeve for accommodating batteries, at the upper end of which a metal sleeve for accommodating a consumer load, such as an electric bulb, is mounted, a guide opening formed in the wall of the grip sleeve, a switching slide being guided the guide opening in a longitudinal direction of the grip sleeve, a contact member extending from a lower end of the grip sleeve with one contact end into the guide opening, and a contact spring member having one end conductively connected to the metal sleeve manner and another free end extending into the guide opening such that the free end is disposed above the contact member and is brought into contact with the contact member by displacing the switching slide. The contact between free end of the contact spring member and the contact member is created by at least two contact points. At least one longitudinal recess is provided in the contact end of the contact member. At least one contact head extending towards the contact member is provided at the free end of the contact spring member for engaging in the longitudinal recess for creating a contact between the contact member and the contact spring member, the contact head being formed such that it contacts both longitudinal sides of the longitudinal recess.

9 Claims, 5 Drawing Sheets

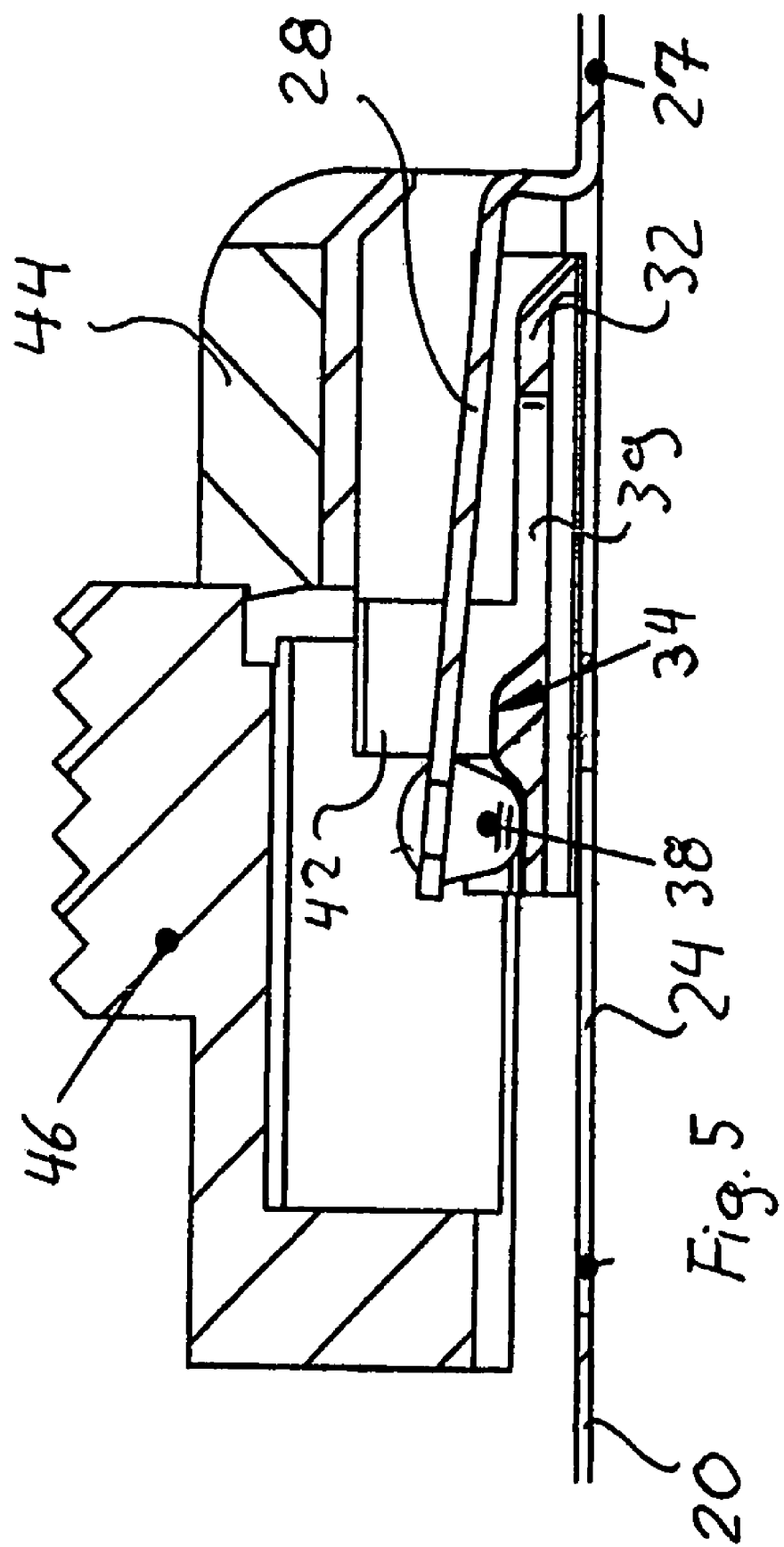

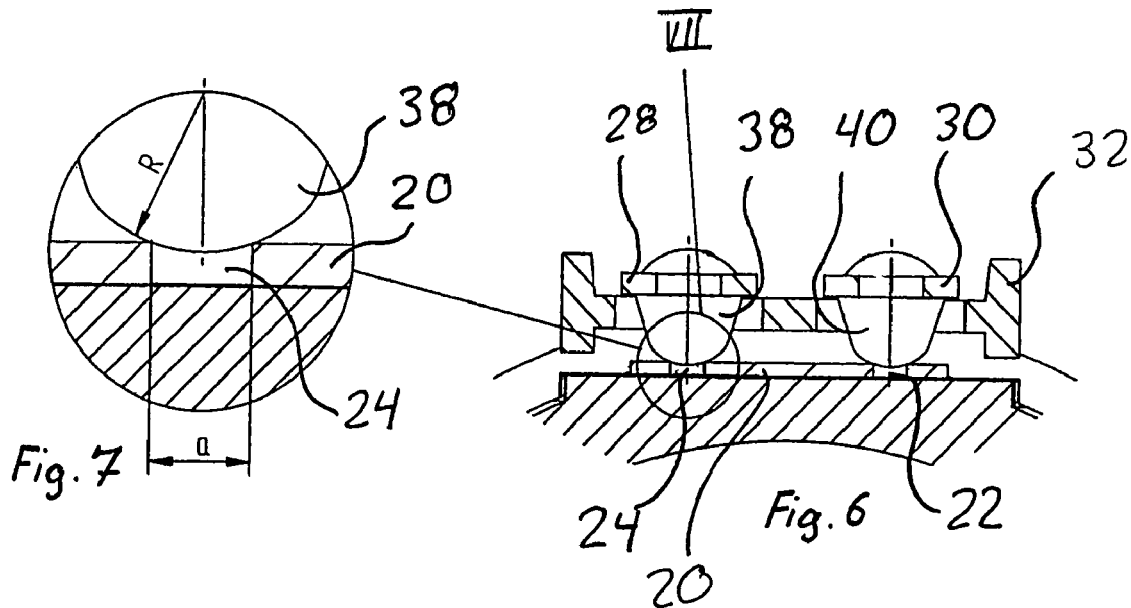
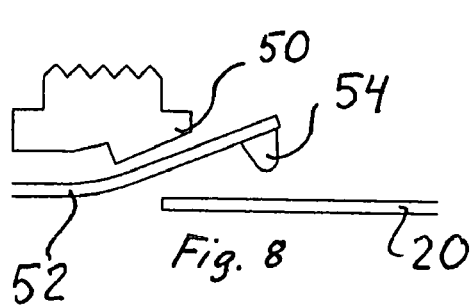
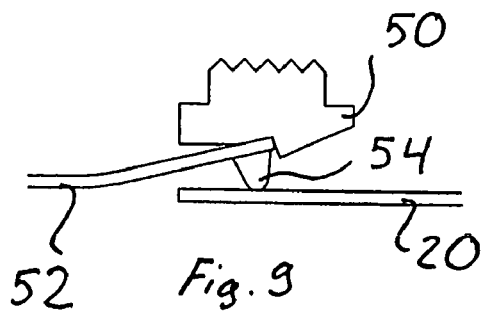
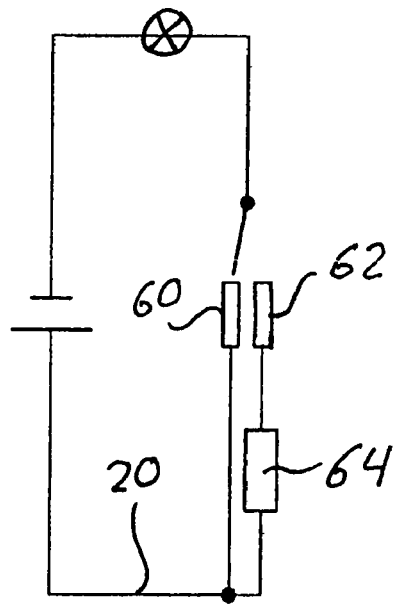

BATTERY GRIP

BACKGROUND OF THE INVENTION

The invention relates to a battery grip for diagnostic units.

Such battery grips, as known, for example, from DE-PS 1 811 923 B, serve as a light source for medical diagnostic instruments, such as otoscopes, ophthalmoscopes etc. A threaded sleeve made of metal, into which an electric bulb is inserted as a consumer load, is disposed at the upper end of a grip sleeve. Batteries or accumulators are arranged in the grip sleeve, the positive poles of which are attached to the electric bulb and the negative poles of which are connected by means of a biased spring, to a contact strip extending upwards along the inner wall of the grip sleeve to a guide opening for a switching slide. A contact spring is fixed in a conducting manner to the threaded sleeve, the free end of the contact spring extending into the guide opening to such an extent that it is disposed above the contact strip. Normally the contact spring is biased such that it is located at a distance to the contact strip while the switching slide is in a circuit-opening position. When the switching slide is moved from its circuit-opening position to its circuit-closing position, it urges the contact spring against the contact strip so that the circuit is closed and the electric bulb illuminates. Both the contact spring member and the contact strip of the known battery grip are formed in the shape of continuous strips so that a line or area contact between the two members is established when the electric bulb is switched on. However, in some cases it turned out that failure might occur in the case of a very high number of switching cycles.

U.S. Pat. No. 4,866,228 discloses a switch having a stationary contact member and a movable contact member, wherein the contact between both is created through several contact points, which are achieved by a finger-like structure of the free end of the contact spring member disposed above the stationary contact member. By this, increased reliability of the switching contact is to be achieved.

The object of the invention is to create a battery grip by means of a simple design the function of which is always guaranteed even in the case of a very high number of switching cycles.

SUMMARY OF THE INVENTION

The foregoing object is achieved by a battery grip comprising a grip sleeve for accommodating batteries, at the upper end of which a metal sleeve for accommodating a consumer load, such as an electric bulb, is mounted; a guide opening formed in the wall of said grip sleeve, a switching slide being guided said guide opening in a longitudinal direction of said grip sleeve; a contact member extending from a lower end of said grip sleeve with one contact end into said guide opening; a contact spring member having one end conductively connected to said metal sleeve manner and another free end extending into said guide opening such that the free end is disposed above said contact member and is brought into contact with said contact member by displacing said switching slide, wherein said contact between free end of said contact spring member and said contact member is created by means of at least two contact points; wherein at least one longitudinal recess is provided in said contact end of the contact member, and at least one contact head extending towards said contact member is provided at said free end of said contact spring member for engaging in said longitudinal recess for creating a contact between said contact member and said contact spring member, said contact head being formed such that it contacts both longitudinal sides of said longitudinal recess.

In the battery grip according to the invention, the contact head of the contact spring member engages in the longitudinal recess of the contact member and in doing so touches the lateral borders of the longitudinal recess. By this, two redundant contact points are created during the contact of a contact head with a contact member.

When the contact spring member has two spring tongues each of which is provided with a contact head and if two longitudinal recesses are formed in the contact member, there are four contact points present during touching, which further increases functional reliability.

In a preferred embodiment, in a circuit-closing position of the switching slide the contact spring member is in biased contact with the contact member. The switching slide is provided with a switching contour, which is formed such that during shifting of the switching slide to a circuit-opening position it comes into contact with the contact head and that it lifts the contact spring member away from the contact member. In this embodiment a continuous contact in the circuit-closing position is guaranteed by the bias of the contact spring.

However, it is also possible to configure the battery grip such that in a circuit-opening position of the switching slide the contact spring member is by its own biasing force, out of contact with the contact member. In this case the switching contour at the switching slide is formed such that during shifting of the switching slide to a circuit-closing position it moves the contact spring member to the direction of the contact member until the contact head contacts the contact member.

In some diagnostic applications, especially ophthalmologic applications, it is reasonable to reduce brightness in order to avoid dazzling the patient. In an embodiment of the battery grip that is suitable for this application, at least two contact portions are formed at the contact end of the contact member. One contact portion is in direct connection with the contact member while the other contact portion is connected to the contact member through a series resistor. A switching contour at a switching slide is formed such that in a first circuit-closing position of the switching slide one contact head contacts one contact portion and in a second circuit-closing position the other contact head contacts the other contact portion. By this, a switch for two brightness levels, which is suitable for a high number of switching cycles, is created by means of a simple design. Even more than two brightness levels may be realized in this way.

Preferably, the contact head at the contact spring member is formed by a contact rivet, the rivet head radius of the contact rivet appropriately being 0.5 mm to 2 mm and the width of the longitudinal recess being not less than 0.3 mm and not more than the rivet head radius.

Depending on the requirement the contact rivet may be made of solid silver or solid silver with hard gold plating and the contact member may be silver-plated or gold-plated in the contact area.

The switching reliability is still further increased when the surface profile of the switching contours along an area over which the corresponding contact head runs has a concave recess, the shape of which is adapted to the cross-sectional profile of the contact head.

BRIEF DESCRIPTION OF THE DRAWINGS

In the following, embodiments of the invention will be described in more detail with reference to the drawings, in which:

FIG. 5 shows a sectional view taken along A-A of FIG. 3, wherein the switching slide is in a circuit-closing position;

FIG. 6 shows a sectional view taken along B-B of FIG. 3;

FIG. 7 shows the detail VII of FIG. 6;

FIG. 8 shows a schematic view of the circuit-opening position in a second embodiment of a battery grip;

FIG. 9 shows a schematic view of the circuit-closing position of the embodiment of FIG. 8;

FIG. 10 shows a circuit diagram of another embodiment of the battery grip having two brightness levels.

DETAILED DESCRIPTION

Figure 1:
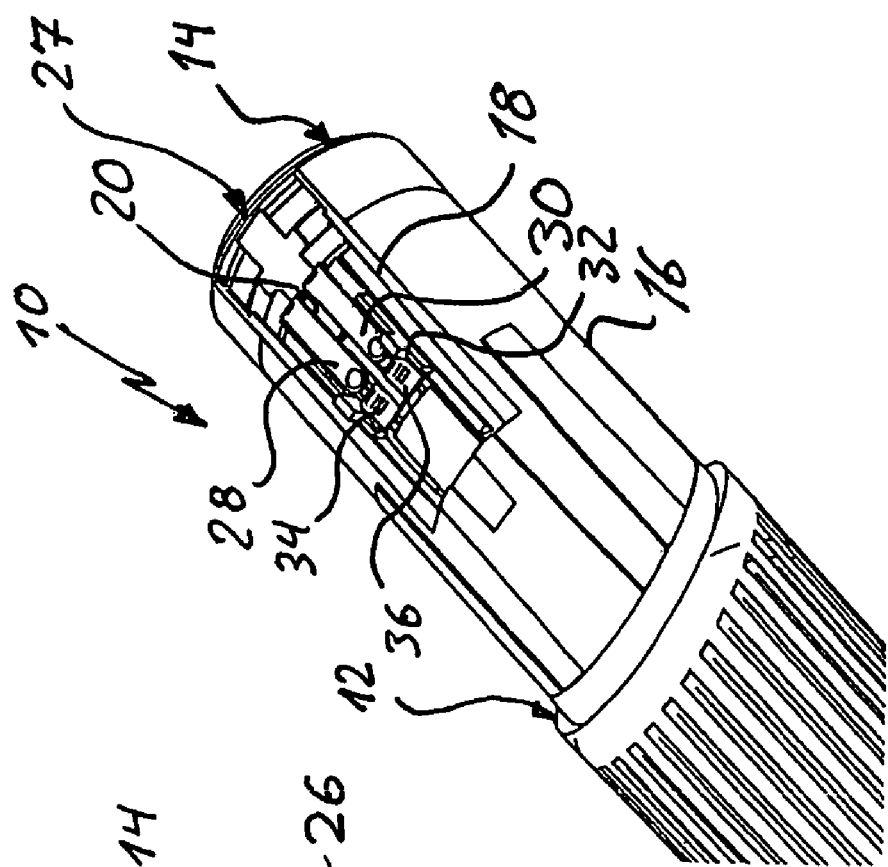
FIG. 1 shows an exploded perspective view of the upper end of a battery grip.
Figure 2:
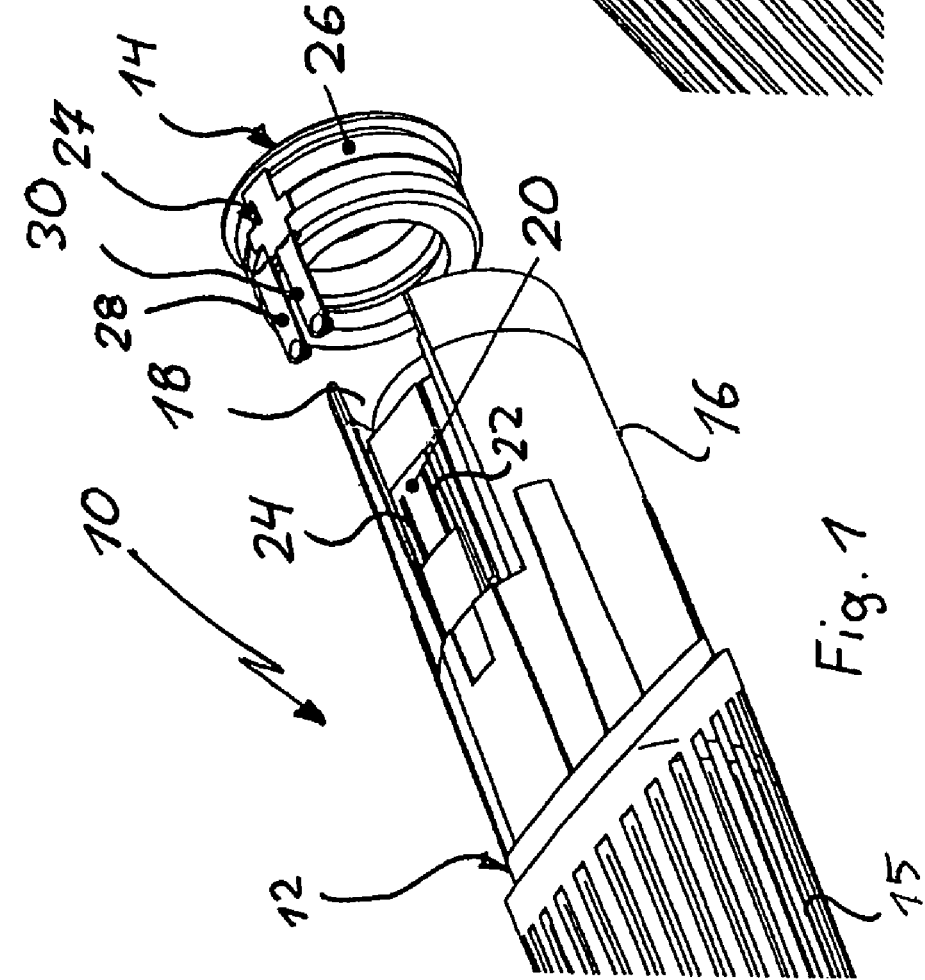
FIG. 2 shows the battery grip of FIG. 1 in an assembled state without end cap.

The first embodiment of the battery grip 10 shown in FIGS. 1 to 7 has a grip sleeve 12 having a lower grip portion 15 and a switch portion 16 at the upper end. An end cap, which is placed upon the upper switch portion 16 in an assembled state and in which a sliding switch 46 is guided in a displaceable manner, is not shown in FIGS. 1 and 2.

As in the prior art known from DE-PS 1 811 923, one or more batteries or one or more accumulators may be inserted into the interior space of the grip sleeve 12. A threaded sleeve 26 made of metal, into which an electric bulb may be inserted such that it is connected with the positive pole of a battery, is screwed into the upper end of the battery grip 10.

In the wall of the switch portion 16 a rectangular guide opening 18 is formed, which is open at the upper border of the switch portion 16.

A contact strip 20 reaches from below into the guide opening 18, the contact strip 20, as in the prior art known from DE-PS 1 811 923, extending to the lower end of the grip sleeve 12 and being connected through a biasing spring (not shown) to the negative pole of a battery in a conducting manner. Two parallelly spaced-apart longitudinal slots 22, 24 are formed in the upper contact end of the contact strip 20 extending into the guide opening 18 in the longitudinal direction of the battery grip 10.

A contact spring 27 is connected in a conducting manner to the threaded sleeve 26, for example, by welding. The contact spring 27 has two parallel spring tongues 28, 30 extending in the longitudinal direction of the battery grip 10 towards the lower end, the free ends of which are disposed above the longitudinal slots 22 and 24, respectively. As can be seen from FIGS. 6 and 7, the free end of each spring tongue 28, 30 is provided with a rivet head 38 and 40, respectively. Depending on the contact requirement—current/voltage—the rivet head radius R of the rivet head may vary from 0.5 mm to 2 mm, wherein the corresponding width a of the corresponding longitudinal slot 22, 24 is to be not less than 0.3 mm and not more than the rivet head radius. Depending on the requirement, the surface of the contact end of the contact member 20 in the area of the longitudinal slots 22, 24 may be silver-plated or gold-plated. The rivet heads 38, 40 may be made of solid silver or solid silver with hard gold plating.

In FIGS. 3, 4, 6 and 7, the sliding switch 46 of the battery grip 10 is in a circuit-closing position, in which the rivet heads 38, 40 contact the contact strip by engaging with their outer ends in the longitudinal slots 24 and 22, respectively, whereby each creates a contact with the longitudinal borders of the longitudinal slots 22 and 24, respectively, at two opposing contact points.

Figure 4:
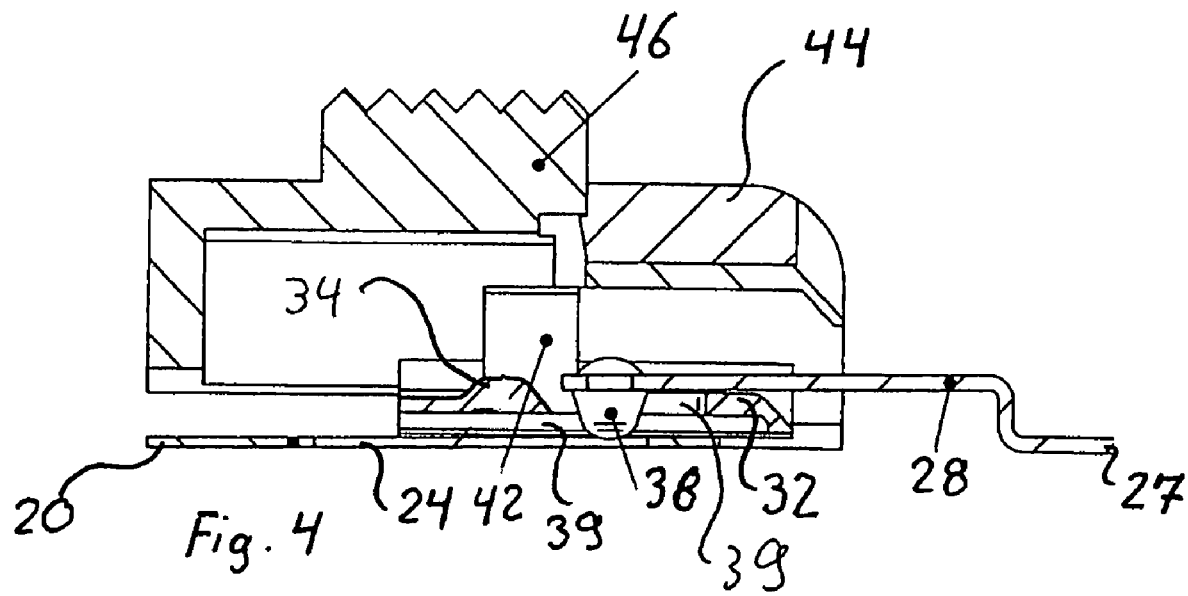
FIG. 4 shows a sectional view taken along A-A of FIG. 3, wherein a switching slide is in a circuit-opening position.
Figure 3:
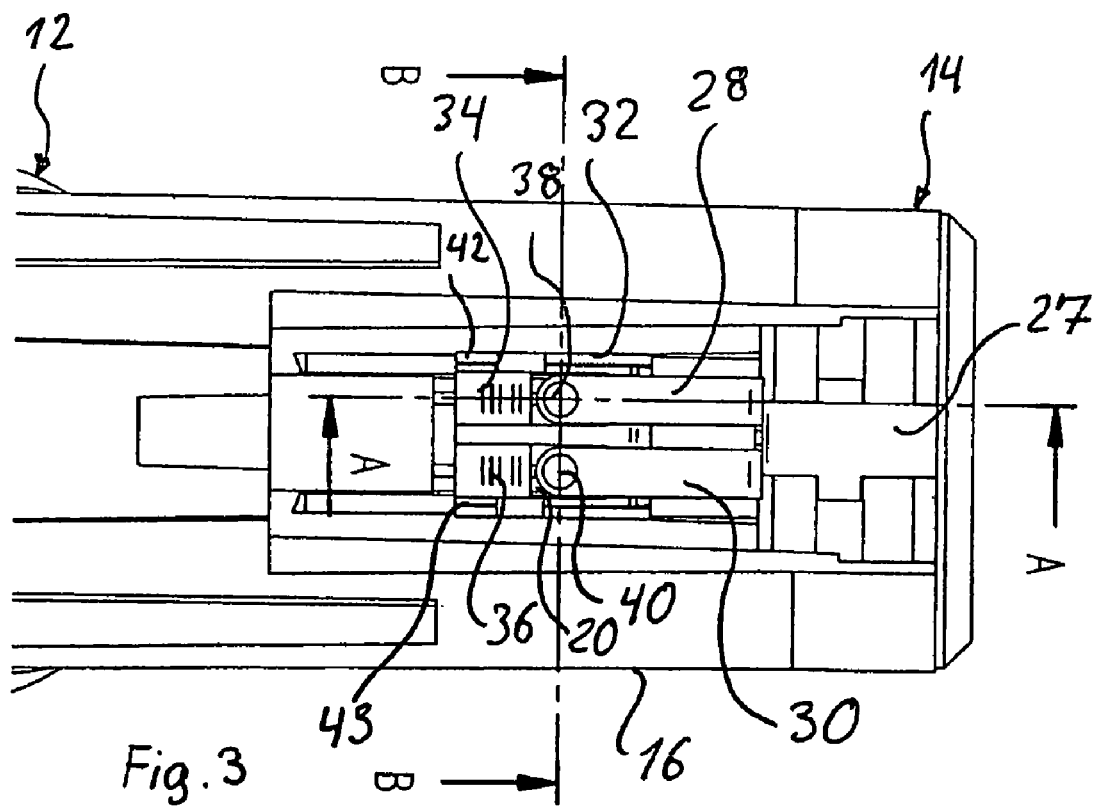
FIG. 3 shows a side view of the upper end of the battery grip.

As can be seen from FIGS. 4 and 6, the rivet heads 38, 40 pass through an opening 39 of a switching slide 32, which is guided in a displaceable manner in the longitudinal direction of the battery grip 10 in the guide opening 18 and is substantially plate-shaped. Switching ridges 42 and 43, respectively, extend upwards from each of the lateral borders of the switching slide 32 and are engaged by the sliding switch 46, which is guided in the longitudinal direction of the battery grip 10. The switching slide 32 is provided with two bump-shaped switching contours 34, 36 each allocated to one of the rivet heads 38, 40 and extending outwards. In the circuit-closing position shown in FIG. 4 the switching contours 34, 36 are located to the left of the rivet heads 38, 40.

For switching off the supply of current to the electric bulb the sliding switch 46 is displaced from the position shown in FIG. 4 upwards (in FIG. 4 to the right) to the position shown in FIG. 5. The sliding switch 46 engages at the switching ridges 42, 43, thereby displacing the switching slide 32 to the same direction. During this, the rivet heads 38, 40 run over the switching contours 34, 36, whereby they are lifted and disengage from the opening 39 and the longitudinal slots 22 and 24, respectively. In doing so, the rivet heads 38, 40 come to lie behind the respective switching contour 34, 36 on the switching slide 32. By this, the contact between the contact springs 28, 30 and the contact strips 20 is interrupted. For switching on the supply of current the sliding switch 46 in FIG. 5 is moved again to the left to the position shown in FIG. 4, whereby the rivet heads 38, 40 run over the respective switching contour 34, 36 until they extend through the opening 39 into the respective longitudinal slots 22, 24 again.

In the embodiment of the battery grip 10 shown in FIGS. 1 to 5 the spring tongues 28, 30 are, by means of their own biasing force, urged with their respective rivet heads 38, 40 into the longitudinal slots 20, 22. FIGS. 8 and 9 are schematic views of another embodiment in which the spring tongues 52 are, by means of their own biasing force, held out of contact with the contact strip 20, their free ends being bent outwards. The switching slide 50 is configured such that during a movement towards the lower end of the battery grip 10 it urges the spring tongues 52 downwards towards the contact strip 20 so that the rivet head 54 is able to engage in the corresponding longitudinal slot. When the switching slide 50 is moved back again from the circuit-closing position shown in FIG. 9 to the circuit-opening position shown in FIG. 8, it comes out of contact with the spring tongue 52, whereby the spring tongue 52, by means of its own biasing force, moves to the original position shown in FIG. 8, which is why the contact between the rivet head 54 and the contact strip 20 is interrupted.

FIG. 10 shows a circuit diagram of another embodiment of a battery grip, in which at the contact end of the contact strip 20 two parallel contact portions 60, 62 are provided, in each of which a longitudinal recess is formed. One contact portion 62 is connected in a conducting manner to the contact strip 20 through a series resistor 64, while the other contact portion 60 is directly connected to the contact strip 20. In this embodiment the switching contours are formed at the switching slide such that in a first circuit-closing position of the switching slide one rivet head contacts one contact portion and in a second circuit-closing position the other rivet head contacts the other contact portion. This enables the setting of two brightness levels.

Figure 11:
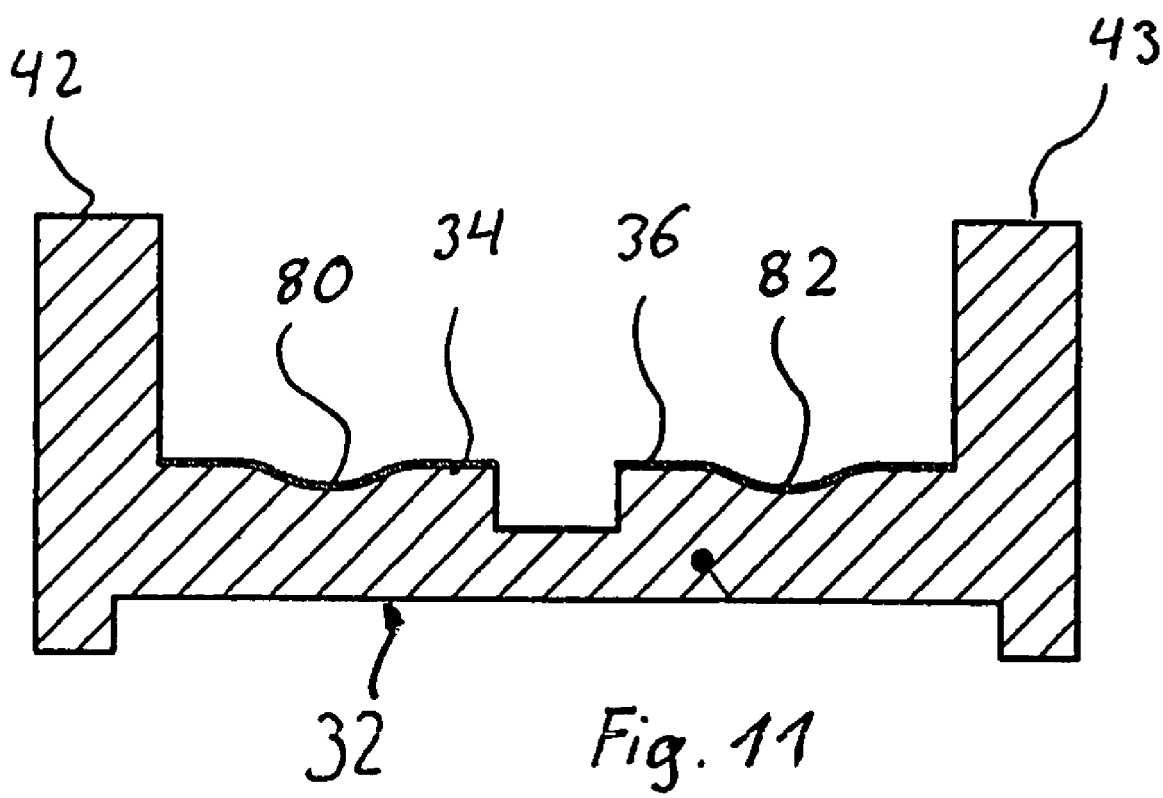
FIG. 11 shows a cross-sectional view of the switching slide.

FIG. 11 shows a preferred modification of the switching slide 32, in which the surface profiles of the switching contours 34, 36 along an area over which the respective rivet head 38, 40 runs have concave recesses 80 and 82, respectively, the shape of which is adapted to the cross-sectional profile of the rivet heads 38 and 40, respectively. By this, the contact area and thus the surface pressure on the switching slide 32 is increased such that wear can be almost completely reduced, which further increases switching reliability.

The invention claimed is:

1. A battery grip for diagnostic units, comprising
   a grip sleeve for accommodating batteries, at an upper end of which is a metal sleeve for accommodating a consumer load;
   a guide opening formed in a wall of said grip sleeve, a switching slide guided in said guide opening in a longitudinal direction of said grip sleeve,
   a contact member extending from a lower end of said grip sleeve and having one contact extending end into said guide opening, and
   a contact spring member having one end conductively connected to said metal sleeve manner and another free end extending into said guide opening such that the free end is disposed above said contact member and is brought into contact with said contact member by displacing said switching slide;
   wherein said contact between free end of said contact spring member and said contact member is created by means of at least two contact points,
   at least one longitudinal recess is provided in said contact end of the contact member, and
   at least one contact head extending towards said contact member is provided at said free end of said contact spring member for engaging in said longitudinal recess for creating a contact between said contact member and said contact spring member, said contact head being formed such that it contacts both longitudinal sides of said longitudinal recess.

2. A battery grip according to claim 1, wherein in a circuit-opening position of said switching slide said contact spring member is out of contact with said contact member and said switching slide is provided with a switching contour, which is formed such that during shifting of said switching slide to a circuit-closing position it moves said contact spring member towards said contact member until said contact head contacts said contact member.

3. A battery grip according to claim 1, wherein at least two contact portions are provided at said contact end of said contact member, one of said contact portions being directly connected to said contact member and another of said contact portions being connected to said contact member through a series resistor, wherein a switching contour is formed such that in a first circuit-closing position of a switching slide one of said contact heads contacts one contact portion and in a second circuit-closing position said other contact head contacts said other contact portion.

4. A battery grip according to claim 1, wherein said contact spring member has two spring tongues, each of which is provided with one of said contact heads, wherein two longitudinal recesses are formed in said contact member.

5. A battery grip according to claim 4, wherein said contact head is formed by a contact rivet.

6. A battery grip according to claim 5, wherein a rivet head radius of said contact rivet is between 0.5 mm to 2 mm and a width of said longitudinal recess is not less than 0.3 mm and not more than said rivet head radius.

7. A battery grip according to claim 6, wherein said contact rivet is made of solid silver or solid silver with hard gold plating and said contact member is silver-plated or gold-plated in said contact area.

8. A battery grip according to claim 1, wherein in a circuit-closing position of said switching slide said contact spring member is in biasing contact with said contact member by means of a corresponding one of said contact heads, and said switching slide is provided with at least one switching contour, which is formed such that during shifting of said switching slide to a circuit-opening position it comes into contact with said corresponding one of said contact heads and said contact spring member is lifted away from said contact member.

9. A battery grip according to of claim 8, wherein a surface profile of said switching contours along an area over which said corresponding contact head runs has a concave recess having a shape which is adapted to a cross-sectional profile of said contact head.

* * * * *